United States Patent [19]

Matsunaga et al.

[11] Patent Number: 5,789,598

[45] Date of Patent: Aug. 4, 1998

[54] PROCESS FOR PRODUCTION OF ALKOXYCARBONYLAMINOTHIAZOLEACETIC ACID DERIVATIVE

[75] Inventors: Tomonori Matsunaga, Tokuyama; Masami Tsuchiya, Kuga-gun, both of Japan

[73] Assignee: Tokuyama Corporation, Yamaguchi-ken, Japan

[21] Appl. No.: 774,294

[22] Filed: Dec. 24, 1996

[30] Foreign Application Priority Data

Dec. 25, 1995 [JP] Japan ................... 7-337440

[51] Int. Cl.$^6$ ........................... C07D 277/593
[52] U.S. Cl. ........................... 548/496
[58] Field of Search ..................... 548/196

[56] References Cited

U.S. PATENT DOCUMENTS 4,386,089  5/1983  Konig et al. ................ 424/246

FOREIGN PATENT DOCUMENTS

| | | |
|---|---|---|
| 0004956 | 10/1979 | European Pat. Off. . |
| 0009008 | 3/1980 | European Pat. Off. . |
| 2826482 | 1/1980 | Germany . |
| 6-128231 | 5/1994 | Japan .................. 548/196 |
| 6-263739 | 9/1994 | Japan .................. 548/196 |
| 6-345736 | 12/1994 | Japan . |

OTHER PUBLICATIONS

*Chemical Abstracts*, vol. 122, No. 21, May 22, 1995, Columbus, Ohio, US; abstract No. 265365s, p. 1104; XP002027281 *abstract * & JP 06 345 736 A (Tokuyama Soda KK) Dec. 20, 1994.

*Database WPI*, Section Ch, week 9651, Derwent Publications Ltd., London, GB; Class B03, AN 96-514979, XP002027282 * abstract * & JP 08 269 025 A (Tokuyama Soda KK), Oct. 15, 1996.

*Primary Examiner*—Robert Gerstl
*Attorney, Agent, or Firm*—Wenderoth, Lind & Ponack, L.L.P.

[57] ABSTRACT

A process for producing an alkoxycarbonylaminothiazoleacetic acid derivative, which comprises reacting an aminothiazoleacetic acid derivative ester with a dialkyl dicarbonate in the presence of a dialkyl carbonate to form an alkoxycarbonylaminothiazoleacetic acid derivative ester, then hydrolyzing the ester with a base, separating the carbonate formed as a by-product, and neutralizing the remaining base.

The process can produce an alkoxycarbonylaminothiazoleacetic acid derivative in a simple operation and safely, at a high yield and at a high reactor yield.

11 Claims, No Drawings

PROCESS FOR PRODUCTION OF ALKOXYCARBONYLAMINOTHIAZOLEACETIC ACID DERIVATIVE

BACKGROUND OF THE INVENTION

(1) Field of the Invention

The present invention relates to a process for producing an alkoxycarbonylaminothiazoleacetic acid derivative advantageously in industry.

(2) Description of the Prior Art

Aminothiazoleacetic acid derivatives [e.g. 2-(2-amino-4-thiazolyl)-2-methoxyiminoacetic acid] are useful as an intermediate for medicine and are used as, for example, the side chain of antibiotic of cephalosporin type or the like. They are reacted, by amidation, with a β-lactam compound (e.g. 7-aminocephalosporanic acid) to become a basic skeleton of a cephalosporin type antibiotic.

In the reaction, a compound obtained by protecting the amino group of an aminothiazoleacetic acid derivative with a certain protecting group is used to prevent the intermolecular reaction between the amino group of the aminothiazoleacetic acid derivative and the carboxyl group of the same compound. The protecting group is preferably an alkoxycarbonyl group (e.g. a t-butoxycarbonyl group) because the protecting group gives an easy protecting reaction and an easy deblocking reaction.

For the synthesis of an amino group-protected aminothiazoleacetic acid derivative, there are known, for example, (1) a process for producing (Z)-2-(2-t-butoxycarbonylamino-4-thiazolyl)-2-methoxyiminoacetic acid by reacting ethyl (Z)-2-(2-amino-4-thiazolyl)-2-methoxyiminoacetate with t-butanol and phosgene to protect the amino group of the ester and then hydrolyzing the reaction product (EP 0009008), and (2) a process for producing (Z)-2-(2-t-butoxycarbonylamino-4-thiazolyl)-2-methoxyiminoacetic acid by reacting 1 equivalent of ethyl (Z)-2-(2-amino-4-thiazolyl)-2-methoxyiminoacetate with 1.3 equivalents of di-t-butyl dicarbonate at 80° C. in t-butanol (solvent) to protect the amino group of the ester and then hydrolyzing the reaction product (DE 2826482).

In producing an alkoxycarbonylaminothiazoleacetic acid derivative by the first process, however, the reaction must be conducted using a special apparatus and with the greatest possible care because virulently poisonous phosgene is used. In the second process, it is necessary to use di-t-butyl dicarbonate in excess of 0.3 equivalent because the reaction is conducted at a high temperature of 80° C. Further, in each of the processes, the ethyl (Z)-2-(2-t-butoxycarbonylamino-4-thiazolyl)-2-methoxyiminoacetate obtained by the protection of amino group is once separated and then subjected to hydrolysis, which invites a lower yield and requires a very complicated operation.

In order to solve these problems, it was reported that when an aminothiazoleacetic acid derivative ester is reacted with a dialkyl dicarbonate in the presence of a particular tertiary amine in a dialkyl carbonate (solvent), alkoxycarbonylation proceeds at a high selectivity under mild conditions [Japanese Patent Application Kokai (Laid-Open) No. 345736/1994].

In producing an alkoxycarbonylaminothiazoleacetic acid derivative by such a process, however, severe foaming takes place in the neutralization step and the surface of the reaction system rises, making it impossible to obtain a high reactor yield (the reactor yield is a yield of intended product in unit volume of a reaction product including the foam generated by the foaming of carbonate and a slurry).

SUMMARY OF THE INVENTION

An object of the present invention is to produce an alkoxycarbonyl aminothiazoleacetic acid derivative at a high reactor yield and safely.

Another object of the present invention is to produce an alkoxycarbonylaminothiazoleacetic acid derivative at a high yield.

The present inventors made an intensive study in order to solve the problems of the prior art. As a result, the present inventors found that the foaming in the above-mentioned neutralization is caused by the carbonate formed mainly by the hydrolysis of dialkyl carbonate (the hydrolysis is a side reaction in the hydrolysis of alkoxycarbonylaminothiazoleacetic acid derivative ester). A further study conducted based on the finding revealed that the above foaming can be solved by separating the above carbonate (by-product) at the completion of the hydrolysis of alkoxycarbonylaminothiazoleacetic acid derivative ester and that the dialkyl carbonate can be efficiently separated in the form of a carbonate. These findings led to the completion of the present invention.

The above objects of the present invention can be achieved by a process for producing an alkoxycarbonylaminothiazoleacetic acid derivative represented by the following formula (III):

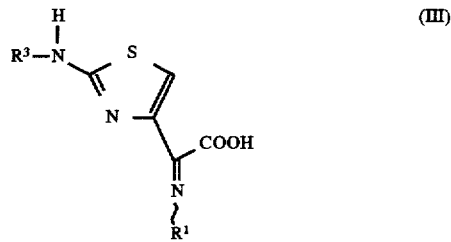

(wherein $R^1$ is a protected hydroxyl group; $R^3$ is an alkoxycarbonyl group; and the bond represented by a wavy line is a syn- or anti-isomer), which process comprises reacting an aminothiazoleacetic acid derivative ester represented by the following general formula (I):

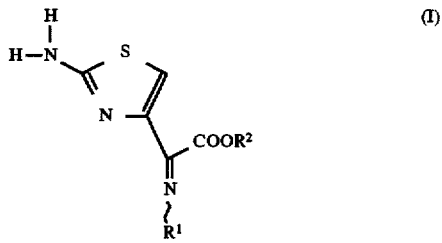

(wherein $R^1$ has the same definition as given above; $R^2$ is an alkyl group; and the bond represented by a wavy line has the same definition as given above) with a dialkyl dicarbonate in a solvent comprising a dialkyl carbonate to form an alkoxycarbonylaminothiazoleacetic acid derivative ester represented by the following formula (II):

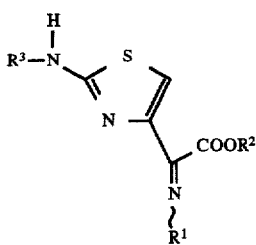

(wherein $R^1$, $R^2$, $R^3$ and the bond represented by a wavy line each have the same definition as given above), then hydrolyzing the alkoxycarbonylaminothiazoleacetic acid derivative ester present in the reaction mixture, with a base in the presence of water, separating the carbonate produced as a by-product in the hydrolysis, and neutralizing the remaining base.

DESCRIPTION OF THE PREFERRED EMBODIMENTS

The aminothiazoleacetic acid derivative ester used in the present invention can be any compound represented by the general formula (I). In the general formula (I), the protected hydroxyl group represented by $R^1$ can be any known protected hydroxyl group and can be exemplified by alkoxy groups such as methoxy group, ethoxy group, n-butoxy group, isobutoxy group, t-butoxy group and the like; substituted alkoxy groups such as methoxymethoxy group, methylthiomethoxy group, methoxyethoxymethoxy group, tetrahydropyranyloxy group, 1-ethoxyethoxy group and the like; aralkyloxy groups such as triphenylmethyloxy group, benzyloxy group and the like; aryloxy groups such as phenoxy group, toluyloxy group and the like; substituted silyloxy groups such as trimethylsilyloxy group, t-butyldimethylsilyloxy group and the like; and carboxyalkoxy groups such as carboxymethoxy group, carboxy-2-propoxy group and the like. Preferable of these are alkoxy groups such as methoxy group, ethoxy group, n-butoxy group, isobutoxy group, t-butoxy group and the like, in view of the stability of the compound represented by the general formula (I).

In the general formula (I), the alkyl group represented by $R^2$ can be any known alkyl group and can be exemplified by methyl group, ethyl group, n-propyl group, isopropyl group, n-butyl group, isobutyl group, t-butyl group, n-pentyl group and cyclohexyl group.

Preferable of these are $C_{1-4}$ alkyl groups such as methyl group, ethyl group, n-propyl group, isopropyl group, n-butyl group, isobutyl group, t-butyl group and the like, in view of, for example, the easy removal of alcohol formed by hydrolysis.

The $R^1$ group of the general formula (I) may be a syn-isomer or an anti-isomer. In the present invention, these isomers may be used singly or in admixture of the two.

Specific examples of the aminothiazoleacetic acid derivative ester of the general formula (I) usable in the present invention are methyl 2-(2-amino-4-thiazolyl)-2-methoxyiminoacetate, ethyl 2-(2-amino-4-thiazolyl)-2-methoxyiminoacetate, isopropyl 2-(2-amino-4-thiazolyl)-2-methoxyiminoacetate, ethyl 2-(2-amino-4-thiazolyl)-2-triphenylmethyloxyiminoacetate, ethyl 2-(2-amino-4-thiazolyl)-2-(1-carboxymethoxy)iminoacetate and ethyl 2-(2-amino-4-thiazolyl)-2-(2-carboxy-2-propoxy)iminoacetate.

In the present invention, the dialkyl dicarbonate reacted with the aminothiazoleacetic acid derivative ester represented by the general formula (I) can be any known dialkyl dicarbonate. Specific examples thereof can be dimethyl dicarbonate, diethyl dicarbonate, diisopropyl dicarbonate, diisobutyl dicarbonate, di-t-butyl dicarbonate and di-t-amyl dicarbonate.

Of these, particularly preferable is di-t-butyl dicarbonate in view of the ease of protecting reaction or deblocking reaction, etc.

The amount of the dialkyl dicarbonate used is not particularly restricted as long as it is at least 1 equivalent per equivalent of the functional group protected (specifically, amino group). It is preferably 1–1.3 equivalents in view of the economy, etc.

The reaction of the aminothiazoleacetic acid derivative ester of the general formula (I), with the dialkyl dicarbonate proceeds without using any catalyst, but generally proceeds more easily in the presence of a tertiary amine catalyst. The catalyst used can be any known tertiary amine compound.

Specific examples of the catalyst preferably used in the present invention are aromatic tertiary amines such as pyridine, 4-N,N-dimethylaminopyridine, 4-N,N-diethylaminopyridine, 4-pyrrolidinopyridine, N,N-dimethylbenzylamine and the like; aliphatic tertiary amines such as triethylamine, tributylamine, N,N,N',N'-tetramethyl-1,3-propanediamine, N,N,N',N'-tetramethyl-1,2-ethylenediamine and the like; and alicyclic tertiary amines such as N-methylmorpholine, 1,4-dimethylpiperazine and the like. Of these, particularly preferable are N,N,N',N'-tetramethyl-1,2-ethylenediamine, N,N,N',N'-tetramethyl-1,2-ethylenediamine, N,N,N',N'-tetraethyl-1,3-propanediamine, N,N-dimethylbenzylamine and 4-N,N-dimethylaminopyridine in view of the selectivity of the alkoxycarbonylation, etc. These catalysts can be used singly or in admixture of two or more.

The amount of the catalyst used per equivalent of the aminothiazoleacetic acid derivative ester of the general formula (I) is not particularly restricted but is preferably 0.0001–0.5 equivalent, more preferably 0.005–0.1 equivalent in view of the yield of intended product, the removal of catalyst after reaction, etc.

The above reaction is conducted ordinarily in a solvent. A dialkyl carbonate is used as the solvent and this is necessary to enhance the selectivity of intended product.

Examples of the dialkyl carbonate used preferably in the present invention are dimethyl carbonate, diethyl carbonate and dipropyl carbonate.

Of these, dimethyl carbonate is particularly preferable because it has a low boiling point and is easy to handle.

The amount of the dialkyl carbonate used must be at least 1 molar equivalent per mole of the aminothiazoleacetic acid derivative ester of the general formula (I). When the amount is smaller than 1 molar equivalent, the selectivity of intended product is low; the amount of the dialkyl carbonate required is larger; and the amount of by-product formed tends to be larger.

The solvent used may be a dialkyl carbonate alone or its mixture with other solvent.

The amount of the solvent (wherein the dialkyl carbonate is an essential component) used is not particularly restricted, but is preferably 30–1,000 parts by weight, more preferably 80–200 parts by weight per 100 parts by weight of the aminothiazoleacetic acid derivative ester of the general formula (I) in view of the easiness of stirring, the economy, etc.

The method for reacting the above raw materials is not particularly restricted, but preferably the dialkyl dicarbonate is added to a suspension of the aminothiazoleacetic acid derivative ester of the general formula (I) and the catalyst in the solvent.

The temperature of the above reaction is not particularly restricted. However, with too low a reaction temperature, the whole system solidifies or no sufficient reaction rate is obtained. With too high a reaction temperature, the dialkyl dicarbonate decomposes. Therefore, the preferable reaction temperature is generally higher than the solidifying point of the reaction system but not higher than 80° C., particularly 0°–50° C.

The reaction can be conducted at any of atmospheric pressure, applied pressure and reduced pressure. The sufficient reaction time is generally 0.1–30 hours although it varies depending upon the reaction temperature used and the kind of the solvent used.

By the above reaction, there can be obtained an alkoxycarbonylaminothiazoleacetic acid derivative ester of the general formula (II).

In the present invention, the alkoxycarbonylaminothiazoleacetic acid derivative ester of the general formula (II) is subjected to hydrolysis without being purified and then neutralized, whereby an alkoxycarbonylaminothiazoleacetic acid derivative represented by the general formula (III) can be obtained easily at a high yield.

When the alkoxycarbonylaminothiazoleacetic acid derivative ester is purified by treatments such as crystallization, acid treatment, silica gel column chromatography, adsorption by adsorbent and the like, the number of steps increase and the treatments bring about a reduced yield and inclusion of the decomposition product of alkoxycarbonylaminothiazoleacetic acid derivative ester.

In the present invention, the alkoxycabonylaminothiazoleacetic acid derivative ester is reacted with a base for hydrolysis, without being purified. The base used for hydrolysis has no restriction. Preferable examples thereof are alkali metal hydroxides such as lithium hydroxide, sodium hydroxide, potassium hydroxide and the like; alkaline earth metal hydroxides such as calcium hydroxide, magnesium hydroxide and the like; alkali metal carbonates such as sodium carbonate, potassium carbonate and the like; and alkali metal bicarbonates such as potassium hydrogencarbonate, sodium hydrogencarbonate and the like. Of these, particularly preferable are sodium hydroxide and potassium hydroxide in view of the favorable reaction time, etc.

The amount of the base used in hydrolysis may be at least 1 equivalent per equivalent of the alkoxycarbonylaminothiazoleacetic acid derivative ester, but is preferably 1–5 equivalents per equivalent of the alkoxycarbonylaminothiazoleacetic acid derivative ester in view of the economy, etc. Since the base is consumed also by the dialkyl carbonate, the amount of the dialkyl carbonate is determined and the base is added in excess so as to be able to decompose the dialkyl carbonate. Specifically, when the solvent used is dimethyl carbonate, the amount of dimethyl carbonate remaining after solvent distillation is determined and the base is added in excess so as to be able to decompose the remaining dimethyl carbonate.

There is no restriction as to the amount of the water used for hydrolysis, but 100–1,000 parts by weight of water is preferably used per 100 parts by weight of the alkoxycarbonylaminothiazoleacetic acid derivative ester in view of the reaction rate, the economy, etc. In the hydrolysis, a new solvent may be added to the reaction mixture after alkoxycarbonylation. Such a solvent for hydrolysis can be any ordinary solvent. Specific examples thereof are alcohols such as methanol, ethanol, propanol and the like; ethers such as diethyl ether, tetrahydrofuran, dioxane and the like; nitriles such as acetonitrile and the like; ketones such as acetone, methyl ethyl ketone and the like; aromatic hydrocarbons such as benzene, toluene and the like; and hydrocarbons such as hexane, heptane, pentane and the like. Of these, particularly preferable are solvents having compatibility with water, such as alcohols (e.g. methanol, ethanol and propanol), ketones (e.g. acetone), nitrites (e.g. acetonitrile) and the like in view of the reaction rate, etc.

These solvents may be used singly or as a mixed solvent of two or more. It is possible that the solvent used in the alkoxycarbonylation is diminished by distillation and a new solvent is added. Complete distillation of the former solvent is difficult and troublesome and, moreover, excessive distillation invites thermal decomposition; therefore, the solvent is distilled off in an amount which can be removed easily and the residual amount is left undistilled.

In the hydrolysis, individual components are contacted with each other without any restriction. For example, an aqueous base solution may be added to the alkoxycarbonylation product, or a base and water may be separately added thereto. Or, the alkoxycarbonylation product may be added to a suspension of a base in water and a solvent.

In the hydrolysis, the reaction temperature is not particularly restricted. However, with too low a reaction temperature, the whole system solidifies or no sufficient reaction rate is obtained. With too high a reaction temperature, the product decomposes. Therefore, the preferable reaction temperature is generally higher than the solidifying point of the reaction system but not higher than 80° C., particularly 0°–60° C.

The reaction can be conducted at any of atmospheric pressure, applied pressure and reduced pressure. The sufficient reaction time is generally 0.1–50 hours although it varies depending upon the reaction temperature used and the kind of the solvent used.

The biggest feature of the present invention is that the carbonate produced as a by-product in the above hydrolysis is separated and, in the subsequent step, the residual base is neutralized. That is, the salt of the alkoxycarbonylaminothiazoleacetic acid, synthesized as above generally contains a carbonate derived from the remaining alkyl carbonate; this carbonate is separated; then, the residual base is neutralized; thereby, formation of carbonic acid gas is effectively diminished and an alkoxycarbonylaminothiazoleacetic acid derivative of the above-general formula (III) can be synthesized at a high reactor yield easily and safely.

In the present invention, separation of the carbonate produced as a by-product can be conducted by any ordinary separation method such as filtration, settling, back extraction or the like. The separation method is hereinafter described specifically. In the filtration, any ordinary filter material can be used. The crystal grain diameter of the carbonate formed in the hydrolysis cannot be specified generally because it varies depending upon the kind, amount and mixing ratio of solvent used, the temperature of hydrolysis, the kind and amount of base used, etc., but it is generally in the range of 1–500 µm. Therefore, the filter material used may have a pore diameter capable of capturing grains of 1 µm or larger in diameter. Specific examples of the filter material are a filter paper, a filter cloth, a membrane filter and a filter plate. The salt produced as a by-product can be easily removed by atmospheric filtration but, in order to shorten the filtration time, it is possible to use, as necessary, pressure filtration, vacuum filtration or centrifugal filtration. The filtration pressure is not particularly restricted because it varies depending upon the grain diameter of carbonate and the pore diameter of filter material; however, in view of the filtration rate, etc., it is preferably 1–10 atm. in the case of pressure filtration and 500 mmHg or less in the case of vacuum filtration. The centrifugal force employed in centrifugal separation is not particularly restricted, either, for the same reason but is generally preferred to be in the range of 10–3,000 G.

In the settling, since the specific gravity of the carbonate produced is generally in the range of 1.4–3.0 g/cm$^3$ although it varies depending upon the reaction conditions employed and the kind of carbonate formed and cannot be generalized, spontaneous sedimentation is sufficient generally. However, centrifugal settling or the like may be used as necessary. The centrifugal force used in settling cannot be specified because it varies depending upon the specific gravity of carbonate, but is preferably in the range of 10–5,000 G. In order to separate carbonate which is produced as a by-product, there may also be employed back extraction.

In the neutralization reaction, it is easy and preferable to use the solution per se after carbonate separation, but a new solvent may be added. Specific examples of the new solvent preferably used are organic solvents such as alcohol (e.g. methanol or ethanol), ether (e.g. tetrahydrofuran or dioxane), amide (e.g. N,N-dimethylformamide), sulfoxide (e.g. dimethyl sulfoxide), nitrile (e.g. acetonitrile) and the like; and an inorganic solvent (water).

In the present invention, the alkoxycarbonylaminothiazoleacetic acid derivative salt obtained is neutralized with an acid. The acid used therefor can be any known acid. Specific examples thereof are inorganic acids such as hydrochloric acid, nitric acid, sulfuric acid, phosphoric acid and the like; and organic acids such as formic acid, acetic acid, citric acid, trifluoroacetic acid, p-toluenesulfonic acid and the like. Of these, hydrochloric acid and sulfuric acid are preferable in view of the easiness of removal after the neutralization, etc.

The amount of the acid used in the present invention is not particularly restricted as long as it can sufficiently neutralize the base present in the reaction system. Too large an amount, however, causes decomposition of the product. Therefore, a preferred amount is such that the pH of the reaction mixture at the completion of neutralization becomes 1–6, preferably 1.5–5.

The temperature of neutralization is not restricted at all. However, with too low a temperature, the solution to be neutralized solidifies. With too high a temperature, the product decomposes. Therefore, the preferable temperature is generally higher than the solidifying point of the solution but not higher than 100° C., particularly higher than the solidifying point of the solution but not higher than 50° C.

In the present invention, the neutralization can be conducted at any of atmospheric pressure, applied pressure and reduced pressure.

The separation of the thus produced alkoxycarbonylaminothiazoleacetic acid derivative is conducted by any known method. The method specifically includes solid-liquid separations such as filtration (e.g. atmospheric filtration, pressure filtration or vacuum filtration), decantation, centrifugal separation and the like; extraction using an organic solvent; and so forth.

Thus, the alkoxycarbonylaminothiazoleacetic acid derivative of the general formula (III) can be produced advantageously and safely in industry without the necessity of ester separation in the course of the process.

In the present invention, use of dialkyl carbonate makes small the amount of dialkyl dicarbonate used, which is economical; the dialkyl carbonate can be removed as a carbonate in the course of the process, which makes unnecessary a complicated operation for separation; after the hydrolysis, the carbonate is removed before the neutralization, whereby the problem of rise of liquid surface in neutralization is eliminated and the alkoxycarbonylaminothiazoleacetic acid derivative of the general formula (III) can be produced safely at a high yield and at a high reactor yield.

The present invention is hereinafter described by way of Examples and Comparative Examples. However, the present invention is not restricted to these Examples.

Example 1

In a four-necked flask was prepared a suspension of 22.9 g (0.1M) of ethyl (Z)-2-(2-amino-4-thiazolyl)-2-methoxyiminoacetate in 25 ml of dimethyl carbonate. To the suspension being stirred at 40° C. were added 0.12 g (1.0 mM) of N,N,N',N'-tetramethyl-1,2-ethylenediamine and 24.0 g (0.11M) of di-t-butyl dicarbonate. The mixture was stirred at room temperature for 15 hours. Thereto were added 50 ml of methanol and a solution of 31.7 g (0.79M) of sodium hydroxide dissolved in 50 ml of water. The mixture was stirred at 40° C. for 15 hours and cooled to room temperature. The resulting crystals were collected by filtration under a vacuum of about 100 mmHg using a filter paper having a pore diameter of 1 μm. The collected crystals were observed using a scanning type electron microscope, which indicated that the crystal grains had a diameter of 50 μm. The crystals were subjected to elemental analysis and atomic absorption spectrometry, which indicated that the crystals were sodium carbonate. The filtrate was neutralized with concentrated hydrochloric acid, which showed substantially no foaming and gave the maximum reaction product volume including the foam and the slurry of 130 ml. The solution was subjected to extraction with ethyl acetate and subsequent vacuum distillation for solvent removal, whereby was obtained 28.1 g (0.093M) of (Z)-2-(2-t-butoxycarbonylamino-4-thiazolyl)-2-methoxyiminoacetic acid at a yield of 93.3%.

Comparative Example 1

Reactions were conducted in the same manner as in Example 1 except that the carbonate crystals were not filtered for removal. In the neutralization, severe foaming took place and the maximum reaction product volume including the foam and the slurry was 1,500 ml.

The product yield was 89.2%.

Examples 2–9

Reactions were conducted in the same manner as in Example 1 except that an aminothiazoleacetic acid derivative ester shown in Table 1 was used as the raw material and a product shown in Table 1 was obtained. The results are shown in Table 1.

TABLE 1

| Example | Aminothiazoleacetic acid derivative ester | Product | Maximum liquid amount in neutralization | Yield |
| --- | --- | --- | --- | --- |
| 2 | Ethyl 2-(2-amino-4-thiazolyl)-2-ethoxyiminoacetate | 2-(2-t-Butoxycarbonylamino-4-thiazolyl)-2-ethoxyiminoacetic acid | 130 ml | 93.5% |
| 3 | Ethyl 2-(2-amino-4-thiazolyl)-2-t-butoxyiminoacetate | 2-(2-t-Butoxycarbonylamino-4-thiazolyl)-2-t-butoxyiminoacetic acid | 130 ml | 92.9% |
| 4 | t-Butyl 2-(2-amino-4-thiazolyl)-2-methoxy-methoxyiminoacetate | 2-(2-t-Butoxycarbonylamino-4-thiazolyl)-2-methoxy-methoxyiminoacetic acid | 130 ml | 93.1% |
| 5 | Ethyl 2-(2-amino-4-thiazolyl)-2-triphenyloxy-iminoacetate | 2-(2-t-Butoxycarbonylamino-4-thiazolyl)-2-triphenyloxyiminoacetic acid | 130 ml | 93.1% |
| 6 | Ethyl 2-(2-amino-4-thiazolyl)-2-benzyloxy-iminoacetate | 2-(2-t-Butoxycarbonylamino-4-thiazolyl)-2-benzyloxyiminoacetic acid | 130 ml | 93.5% |
| 7 | n-Butyl 2-(2-amino-4-thiazolyl)-2-phenoxy-iminoacetate | 2-(2-t-Butoxycarbonylamino-4-thiazolyl)-2-phenoxyiminoacetic acid | 130 ml | 93.3% |
| 8 | Ethyl 2-(2-amino-4-thiazolyl)-2-carboxy-2-propoxyiminoacetate | 2-(2-t-Butoxycarbonylamino-4-thiazolyl)-2-carboxy-2-propoxyiminoacetic acid | 130 ml | 92.9% |

Examples 9–11

Reactions were conducted in the same manner as in Example 1 except that a compound shown in Table 2 was used as the dialkyl dicarbonate and a product shown in Table 2 was obtained. The results are shown in Table 2.

TABLE 2

| Example | Dialkyl dicarbonate | Product | Maximum liquid volume in neutralization | Yield |
| --- | --- | --- | --- | --- |
| 9 | Dimethyl dicarbonate | 2-(2-Methoxycarbonylamino-4-thiazolyl)-2-methoxyiminoacetic acid | 130 ml | 91.9% |
| 10 | Diethyl dicarbonate | 2-(2-Ethoxycarbonylamino-4-thiazolyl)-2-methoxyiminoacetic acid | 130 ml | 92.1% |
| 11 | Diisoproply dicarbonate | 2-(2-Isopropoxycarbonylamino-4-thiazolyl)-2-methoxyiminoacetic acid | 130 ml | 92.2% |

Example 12

Reactions were conducted in the same manner as in Example 1 except that diethyl carbonate was used as the dialkyl carbonate. In the neutralization, there was substantially no foaming and the maximum reaction product volume including the foam and the slurry was 130 ml. The subsequent treatment was conducted in the same manner as in Example 1 to obtain (Z)-2-(2-t-butoxycarbonylamino-4-thiazolyl)-2-methoxyiminoacetic acid at a yield of 93.1%.

Example 13

In a four-necked flask was prepared a suspension of 22.9 g (0.1M) of ethyl (Z)-2-(2-amino-4-thiazolyl)-2-methoxyiminoacetate in 25 ml of dimethyl carbonate. To the suspension being stirred at 40° C. were added 0.12 g (0.11 mM) of N,N,N',N'-tetramethylenediamine and 24.0 g (0.11M) of di-t-butyl dicarbonate. The mixture was stirred at room temperature for 15 hours for a reaction. After the completion of the reaction, dimethyl carbonate was removed by room temperature distillation under a vacuum of 10 mmHg. The distilled dimethyl carbonate was 21.0 g and the remaining dimethyl carbonate was 5.7 g. To the reaction mixture were added 50 ml of methanol and a solution of 12.8 g (0.32M) of sodium hydroxide dissolved in 50 ml of water. The mixture was stirred at 40° C. for 15 hours and cooled to room temperature. The resulting crystals were collected by pressure filtration (a nitrogen pressure of about 1.5 atm.) using a filter paper having a pore diameter of 1 μm, and washed with 20 ml of methanol. The washings were combined with the filtrate, and the mixture was subjected to vacuum concentration under the conditions of 60 mmHg and 40° C. to obtain a total weight of 91.1 g. 340 ml of water was added thereto. The resulting solution was neutralized with concentrated hydrochloric acid, which showed substantially no foaming and gave the maximum reaction product volume including the foam and the slurry of 430 ml. The solid precipitated by the neutralization was collected by centrifugation, washed with 250 ml of water, and vacuum-dried at 40° C. to obtain 27.8 g (0.092M) of (Z)-2-(2-t-butoxycarbonylamino-4-thiazolyl)-2-methoxyiminoacetic acid at a yield of 92.3%.

What is claimed is:

1. A process for producing an alkoxycarbonylaminothiazoleacetic acid derivative represented by the following formula (III):

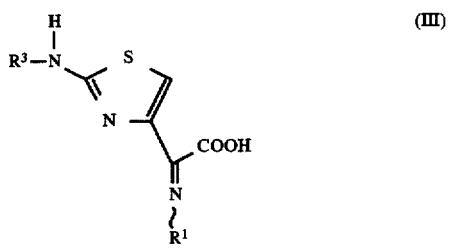

(wherein $R^1$ is a protected hydroxyl group; $R^3$ is an alkoxycarbonyl group; and the bond represented by a wavy line is a syn- or anti-isomer), which process comprises reacting an aminothiazoleacetic acid derivative ester represented by the following general formula (I):

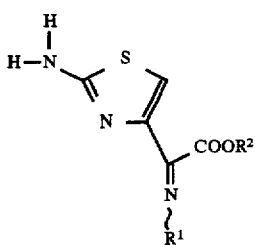

(I)

(wherein $R^1$ has the same definition as given above; $R^2$ is an alkyl group; and the bond represented by a wavy line has the same definition as given above) with a dialkyl dicarbonate in a solvent comprising a dialkyl carbonate to form an alkoxycarbonylaminothiazoleacetic acid derivative ester represented by the following formula (II):

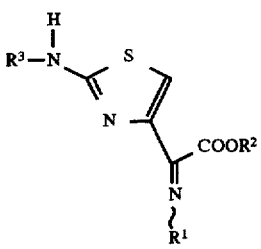

(II)

(wherein $R^1$, $R^2$, $R^3$ and the bond represented by a wavy line each have the same definition as given above), then hydrolyzing the alkoxycarbonylaminothiazoleacetic acid derivative ester present in the reaction mixture, with a base in the presence of water, separating the carbonate produced as a by-product in the hydrolysis, and neutralizing the remaining base.

2. A process according to claim 1, wherein the dialkyl dicarbonate is di-t-butyl dicarbonate.

3. A process according to claim 1, wherein the amount of the dialkyl dicarbonate used is 1–1.3 equivalents per equivalent of the amino group of the aminothiazoleacetic acid derivative ester represented by the general formula (I).

4. A process according to claim 1, wherein the temperature of the reaction for formation of an alkoxycarbonylaminothiazoleacetic acid derivative ester is higher than the solidifying point of the reaction system but not higher than 80° C.

5. A process according to claim 1, wherein the alkoxycarbonylaminothiazoleacetic acid derivative ester represented by the general formula (II) is hydrolyzed without being purified.

6. A process according to claim 1, wherein the base is an alkali metal hydroxide, an alkaline earth metal hydroxide, an alkali metal carbonate or an alkali metal bicarbonate.

7. A process according to claim 1, wherein the amount of the base used is 1-5 equivalents per equivalent of the alkoxycarbonylaminothiazoleacetic acid derivative ester represented by the general formula (II).

8. A process according to claim 1, wherein the hydrolysis is conducted in the presence of water of 100–1,000 parts by weight per 100 parts by weight of the alkoxycarbonylaminothiazoleacetic acid derivative ester represented by the general formula (II).

9. A process according to claim 1, wherein the hydrolysis is conducted at a temperature higher than the solidifying point of the reaction system but not higher than 80° C.

10. A process according to claim 1, wherein the separation of carbonate is conducted by filtration, settling or back extraction.

11. A process according to claim 1, wherein the neutralization is conducted so that the pH of the reaction system becomes 1–6.

* * * * *